US011213197B2

(12) United States Patent
Wang et al.

(10) Patent No.: US 11,213,197 B2
(45) Date of Patent: Jan. 4, 2022

(54) ARTIFICIAL NEURAL NETWORK AND SYSTEM FOR IDENTIFYING LESION IN RETINAL FUNDUS IMAGE

(71) Applicants: SHENZHEN SIBIONICS TECHNOLOGY CO., LTD., Shenzhen (CN); SHENZHEN SIBRIGHT TECHNOLOGY CO., LTD., Shenzhen (CN)

(72) Inventors: Juan Wang, Shenzhen (CN); Bin Xia, Shenzhen (CN); Yujing Bai, Shenzhen (CN); Xiaoxin Li, Shenzhen (CN); Zhigang Hu, Shenzhen (CN); Yu Zhao, Shenzhen (CN)

(73) Assignees: Shenzhen Sibionics Technology Co., Ltd., Shenzhen (CN); Shenzhen Sibright Technology Co., Ltd., Shenzhen (CN)

( * ) Notice: Subject to any disclaimer, the term of this patent is extended or adjusted under 35 U.S.C. 154(b) by 136 days.

(21) Appl. No.: 16/609,213

(22) PCT Filed: Aug. 4, 2017

(86) PCT No.: PCT/CN2017/095909
§ 371 (c)(1),
(2) Date: Oct. 29, 2019

(87) PCT Pub. No.: WO2018/201632
PCT Pub. Date: Nov. 8, 2018

(65) Prior Publication Data
US 2020/0085290 A1    Mar. 19, 2020

(30) Foreign Application Priority Data

May 4, 2017  (CN) .......................... 201710306096.8

(51) Int. Cl.
*A61B 3/00* (2006.01)
*G06N 20/20* (2019.01)
(Continued)

(52) U.S. Cl.
CPC ......... *A61B 3/0025* (2013.01); *G06N 3/0454* (2013.01); *G06N 3/08* (2013.01);
(Continued)

(58) Field of Classification Search
CPC ...... A61B 3/0025; G06N 20/20; G06N 20/10; G06N 3/0454; G06N 3/08; G06T 7/0012;
(Continued)

(56) References Cited

U.S. PATENT DOCUMENTS 10,610,098 B1 *  4/2020  Soliz ..................... G06K 9/0061
2015/0125052 A1 *  5/2015  Wong .................... G06K 9/4642
382/128

(Continued)

*Primary Examiner* — Khai M Nguyen
(74) *Attorney, Agent, or Firm* — Avant Law Group, LLC (57) ABSTRACT

The present disclosure provides an artificial neural network system for identifying a lesion in a retinal fundus image that comprises a pre-processing module configured to separately pre-process a target retinal fundus image and a reference retinal fundus image taken from a same person; a first neural network (12) configured to generate a first advanced feature set from the target retinal fundus image; a second neural network (22) configured to generate a second advanced feature set from the reference retinal fundus image; a feature combination module (13) configured to combine the first advanced feature set and the second advanced feature set to form a feature combination set; and a third neural network (14) configured to generate, according to the feature combination set, a diagnosis result. By using a target retinal fundus image and a reference retinal fundus image as independent input information, the artificial neural network may simulate a doctor, determining lesions on the target (Continued)

retinal fundus image using other retinal fundus images from the same person as a reference, thereby enhancing the diagnosis accuracy.

13 Claims, 8 Drawing Sheets

(51) Int. Cl.
*G06N 20/10* (2019.01)
*G06N 3/04* (2006.01)
*G06N 3/08* (2006.01)
*G06T 7/00* (2017.01)

(52) U.S. Cl.
CPC ............. *G06N 20/10* (2019.01); *G06N 20/20* (2019.01); *G06T 7/0012* (2013.01); *G06T 2207/20081* (2013.01); *G06T 2207/20084* (2013.01); *G06T 2207/30041* (2013.01); *G06T 2207/30096* (2013.01)

(58) Field of Classification Search
CPC . G06T 2207/20081; G06T 2207/20084; G06T 2207/30041; G06T 2207/30096
See application file for complete search history.

(56) References Cited

U.S. PATENT DOCUMENTS

2017/0112372 A1* 4/2017 Chakravorty ...... G06K 9/00617
2020/0349710 A1* 11/2020 Paschalakis ......... G06K 9/6269

* cited by examiner

ARTIFICIAL NEURAL NETWORK AND SYSTEM FOR IDENTIFYING LESION IN RETINAL FUNDUS IMAGE

FIELD OF THE INVENTION

The present disclosure relates to the field of artificial neural networks, and more particularly to an artificial neural network and an artificial neural network system for identifying a lesion in a retinal fundus image.

BACKGROUND OF THE INVENTION

An artificial neural network is a machine learning model that simulates the human brain structure. With the development of artificial neural networks, especially artificial intelligence technology such as deep learning, the application of artificial neural networks in the field of medical imaging diagnosis is drawing more and more attention. By using such an artificial neural network, potential lesions can be automatically determined based on medical images, i.e., automatic screening can be done on the medical images. For example, artificial neural networks such as deep learning have been studied in various fields, such as breast cancer pathological analysis, lung cancer detection, cardiovascular imaging and the like.

Medical images, which are usually obtained by means of a camera, an x-ray transmission machine, CT, OCT, MRI and the like, may contain numerous details of body structures or tissues, and identifying such details in a medical image may assist a doctor with relevant diagnosis. Taking retinal fundus images among medical images for example, a retinal fundus image contains abundant details of vitreous body, retinal, choroid and the like, and if there are related lesions, changes such as microangioma, bleeding, hard exudates and the like will be presented in the retinal fundus image. Among those lesions, diabetic retinopathy, for example, as a common retinal fundus lesion, is one of the diabetic complications, and has become one of the main causes of blindness of the working-age population. It is estimated there are 92.4 million diabetic patients in China with a five-year incidence of 43% and a blindness rate of 10%. Various researches indicate that early diagnosis and treatment of the diabetic retinopathy can effectively control or even alleviate the visual impairment of a patient. Therefore, regular retinal fundus disease screening in diabetic patients is important to our society. However, conventional diabetic retinopathy screening requires specialized ophthalmologists to observe retinal fundus images by eyes to make a diagnosis, resulting in high work load and cost, which is not good for the applications in a large scale. Meanwhile, retinal fundus screening requires a doctor to read a large number of retinal fundus images in a short time, and may be too tired to keep the diagnosis accuracy at a high level. Therefore, there is an urgent need for the computer-based automatic screening (automatic image reading) using artificial intelligence algorithms.

At present, such researches have been done or being carried out by scientific research teams. For example, non-patent document 1 discloses a method for diagnosing diabetic retinopathy by artificial intelligence, where a well-known deep learning network structure, Inception-v3, is used, and a high accuracy is achieved. It at least achieves the effect of replacing part of a professional ophthalmologist's work.

In addition, patent document 2 discloses a method, a device and a system for processing a retinal fundus image based on deep learning. In the patent document 2, a conventional convolutional neural network is employed to analyze an image. In particular, a resampled retinal fundus image is input, and a seven-layer convolutional neural network containing five convolutional layers and two fully connected layers is employed for identification.

REFERENCE DOCUMENTS

Non-patent document 1: Development And Validation Of A Deep Learning Algorithm For Detection Of Diabetic Retinopathy In Retinal Fundus Photographs, JAMA Nov. 29, 2016.

Patent document 2: Chinese patent application CN106408564A.

SUMMARY OF INVENTION

However, in the prior art as described above, although deep learning methods have been employed to automatically identify various lesions of diabetic retinopathy using retinal fundus images, such methods are not ready for clinical applications. For example, the Inception-v3 deep learning network structure employed in the method described in the non-patent document 1 is a network structure for natural image classification and target detection that requires an input image to be 299×299 pixels, rather than particular medical images.

In addition, although the patent document 2 also relates to the processing of a retinal fundus image, the purpose thereof is merely identifying regional image features rather than diagnosing retinal fundus diseases. Therefore, the retinal fundus image processing method employed in the patent document 2 is far below the clinical standard.

In view of the technical shortcomings mentioned above, the present disclosure aims to provide an artificial neural network and an artificial neural network system for identifying a lesion in a retinal fundus image that can improve the accuracy of diagnosis of lesions in fundus images.

To this end, an aspect of the present disclosure provides an artificial neural network for identifying a lesion in a retinal fundus image, comprising a pre-processing module configured to separately pre-process a target retinal fundus image and a reference retinal fundus image taken from a same person; a first neural network configured to generate a first advanced feature set from the target retinal fundus image; a second neural network configured to generate a second advanced feature set from the reference retinal fundus image; a feature combination module configured to combine the first advanced feature set and the second advanced feature set to form a feature combination set; and a third neural network configured to generate, according to the feature combination set, a diagnostic conclusion.

In one aspect of the present disclosure, by using a target retinal fundus image and a reference retinal fundus image as separate independent input information, the artificial neural network may simulate a doctor, determining lesions on the target retinal fundus image using other retinal fundus images from the same person as a reference, thereby enhancing the diagnosis accuracy.

Moreover, in the artificial neural network according to one aspect of the present disclosure, the target retinal fundus image and the reference retinal fundus image may be the same image. In this case, even though only one retinal fundus image is used, a valid and reliable diagnostic conclusion may be also obtained.

Moreover, in the artificial neural network according to one aspect of the present disclosure, the first neural network and the second neural network may be the same. In this case, less neural network parameters will be involved, thereby improving the training efficiency of the neural network and preventing over-fitting.

Moreover, in the artificial neural network according to one aspect of the present disclosure, optionally, the pre-processing module comprises an area detection unit configured to detect specified retinal fundus areas in the target retinal fundus image and the reference retinal fundus image; an adjustment unit configured to clip and resize the target retinal fundus image and the reference retinal fundus image; and a normalization unit configured to normalize the target retinal fundus image and the reference retinal fundus image. Thus, the target retinal fundus image and the reference retinal fundus image can be effectively pre-processed, and the subsequent image feature extraction can be performed by each neural network with improved accuracy, thus improving the lesion diagnosis.

Moreover, in the artificial neural network according to one aspect of the present disclosure, optionally, the third neural network generates the diagnosis conclusion based on the feature combination set and patient information. Thus, the process may be more similar to an actual diagnostic process of a real doctor so that the accuracy of diagnosis can be improved. Further, the third neural network may comprise a fully connected layer, and the patient information may be used as an input to the fully connected layer.

Moreover, in the artificial neural network according to one aspect of the present disclosure, optionally, the patient information comprises at least one of age, gender, eyesight, and medical history. In addition, the patient information may also comprise body weight. In this case, the diagnosis is more like the diagnostic process of a real doctor and the accuracy of lesion diagnosis can be improved.

Moreover, in the artificial neural network according to one aspect of the present disclosure, optionally, the first neural network and the second neural network are convolutional neural networks. In this case, taking advantages of both weight-sharing and local receptive view of the convolutional neural network, training of parameters can be greatly reduced, thereby speeding the process and decreasing hardware cost.

In addition, another aspect of the present disclosure provides an artificial neural network for identifying a lesion in a medical image, comprising a pre-processing module configured to separately pre-process a target medical image and a reference medical image taken from one person; a first neural network configured to generate a first advanced feature set from the target medical image; a second neural network configured to generate a second advanced feature set from the reference medical image; a feature combination module configured to combine the first advanced feature set and the second advanced feature set to form a feature combination set; and a third neural network configured to generate a diagnostic conclusion from feature combination set.

In another aspect of the present disclosure, by using a target medical image and a reference medical image as separate independent input information, the artificial neural network may simulate a doctor, determining lesions on the target medical image using other medical images from the same person as a reference, thereby enhancing the diagnosis accuracy.

In the artificial neural network according to another aspect of the present disclosure, optionally, the target medical image and the reference medical image are the same. In this case, even though only one medical image of one person is used, the neural network can be effectively trained and lesion diagnosis can be improved.

In addition, a further another aspect of the present disclosure provides an artificial neural network system comprising a plurality of artificial neural networks as described above; and a diagnostic device configured to combine the diagnostic conclusions output from the plurality of artificial neural networks and output a final diagnostic conclusion.

Still further, another aspect of the present disclosure further provides a method for identifying a lesion in a retinal fundus image, comprising separately pre-processing a pair of retinal fundus images, wherein the image pair contains a target retinal fundus image and a reference retinal fundus image; studying the target retinal fundus image and the reference retinal fundus image by deep learning to obtain features of the target retinal fundus image and features of the reference retinal fundus image; combining the features of the target retinal fundus image with the features of the reference retinal fundus image to form a feature sequence; identifying the feature sequence by deep learning to obtain a diagnostic conclusion. Therefore, the method may simulate a doctor determining lesions on the target retinal fundus image using other retinal fundus images from the same person as a reference, thereby enhancing the diagnosis accuracy.

Moreover, in the method for identifying a lesion in a retinal fundus image according to another aspect of the present disclosure, optionally, the pre-processing step comprises area identification, image clipping, resizing and normalization.

Moreover, in the method for identifying a lesion in a retinal fundus image according to another aspect of the present disclosure, optionally, the pre-processing step also comprises retinal fundus image data expansion during training.

According to the present disclosure, disclosed are an artificial neural network and an artificial neural system for identifying a lesion in a retinal fundus image with improved screening accuracy, and a method for identifying a lesion in a retinal fundus image.

BRIEF DESCRIPTION OF THE DRAWINGS

FIGS. 1A and 1B are retinal fundus images according to a first embodiment of the present disclosure, wherein FIG. 1A shows an exemplary image of normal retinal fundus, and FIG. 1B shows an exemplary image of abnormal retinal fundus.

FIGS. 2A and 2B retinal fundus images with retinal fundus lesions according to the first embodiment of the present disclosure, wherein FIG. 2A shows an exemplary image of retinal fundus with diabetic retinopathy, and FIG. 2B shows an exemplary image of retinal fundus with hypertensive retinopathy.

DETAILED DESCRIPTION OF THE INVENTION

Hereinafter, preferred embodiments of the present disclosure will be described in detail with reference to the accompanying drawings. In the following description, the same components are denoted by the same reference numerals, and the description thereof will not be repeated. In addition, the drawings are merely schematic views, and the ratio of the dimensions of the components to each other or the shape of the components may be different from the actual ones.

It should be noted that the terms "comprising" and "having", and any variants thereof, such as a process, method, system, product, or device, which are included or have a series of steps or units, are not necessarily limited to those steps or units are provided, but may include or have other steps or units not explicitly listed or inherent to such processes, methods, products or devices.

In addition, the subtitles and the like referred to in the following description of the present disclosure are not intended to limit the content or scope of the present disclosure, but merely serve as a hint for reading. Such a subtitle cannot be understood as content for segmenting an article, nor should the content under the subtitle be limited to the scope of the subtitle.

The present disclosure relates to an artificial neural network and an artificial neural network system for identifying a lesion in a retinal fundus image with improved screening accuracy. Processing retinal fundus images by deep neutral networks, such as a convolutional neural network, have been found in the prior art (see the above non-patent document 1 and patent document 2). However, as mentioned above, Inception-v3 is a network structure directed against natural image classification and target detection rather than particular medical images. Thus, there is still great room for improvement in accuracy on clinical lesion screening from retinal fundus images, such as diabetic retinopathy screening and the like. In addition, the retinal fundus image processing method employed in the above patent document 2 is not good enough for clinical use.

In contrast, in the present disclosure, a target retinal fundus image and a reference retinal fundus image (which two are hereinafter referred to as "a retinal fundus image pair" sometimes) are separately used as independent input information. That is, in the recognition of retinal fundus lesions in a "target retinal fundus image", a "reference retinal fundus image" of the same person is used as a reference, the retinal fundus lesions can be accurately and comprehensively determined. Here, the "target retinal fundus image" refers to a retinal fundus image in need of diagnosis for whether a lesion is present or what kind of lesion is present, while the "reference retinal fundus image" refers to a retinal fundus image that is taken from the same person together with the "target retinal fundus image". In the present disclosure, by using a target retinal fundus image and a reference retinal fundus image simultaneously, the artificial neural network may simulate an actual diagnostic process of a doctor, thereby improving the accuracy of retinal fundus lesion diagnosis.

First Embodiment

Figure 1A:
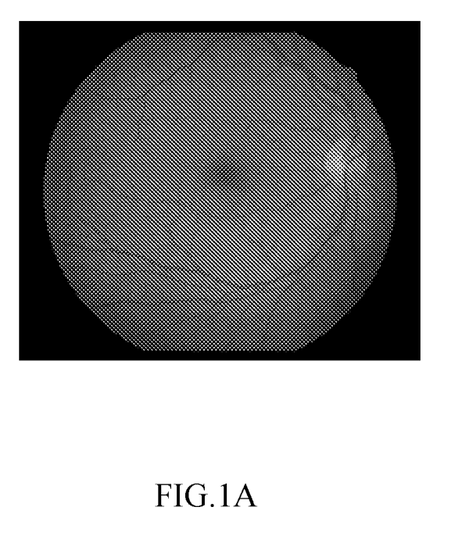
Figure 1B:
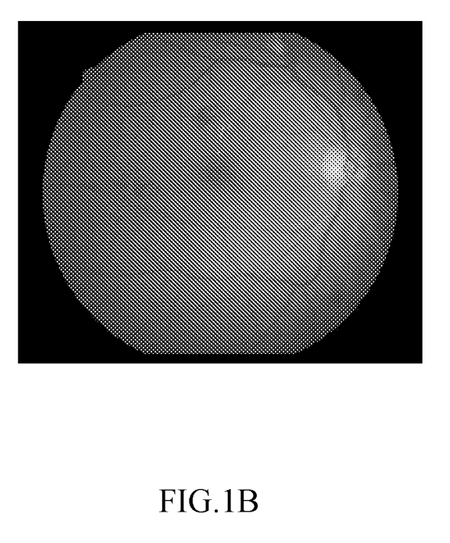
Figure 2A:
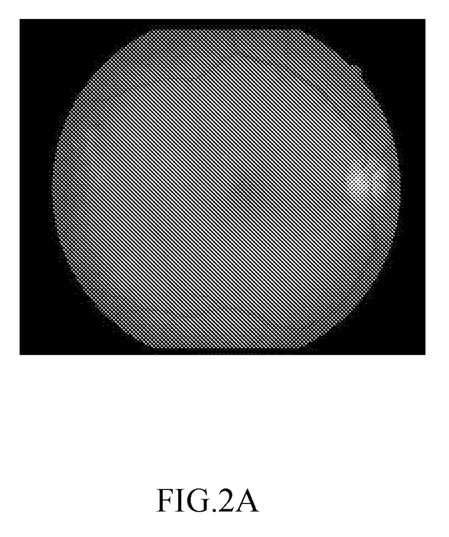
Figure 2B:
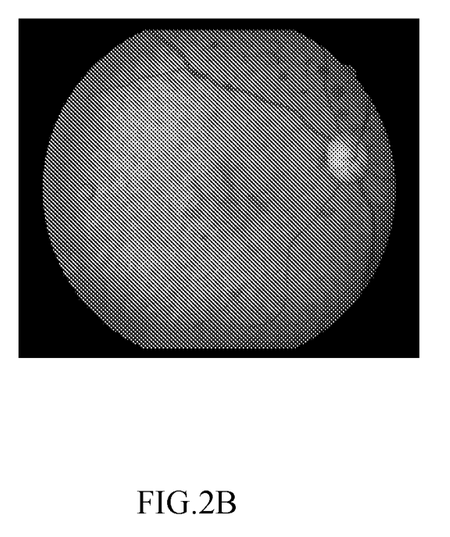

FIG. 1 is a schematic diagram illustrating lesions in retinal fundus images according to a first embodiment of the present disclosure, wherein FIG. 1(*a*) shows an exemplary image of normal retinal fundus, and FIG. 1(*b*) shows an exemplary image of abnormal retinal fundus. FIG. 2 is a schematic diagram illustrating retinal fundus images with retinal fundus lesions according to the first embodiment of the present disclosure, wherein FIG. 2(*a*) shows an exemplary image of retinal fundus with diabetic retinopathy, and FIG. 2(*b*) shows an exemplary image of retinal fundus with hypertensive retinopathy.

In this embodiment, an artificial neural network and an artificial neural network system according to this embodiment systematically study lesion-free retinal fundus images (see FIG. 1(*a*)) and retinal fundus images with lesions (see FIG. 1(*b*)), and become capable of determining whether a lesion is present in a retinal fundus image. In addition, in this embodiment, the artificial neural network and the artificial neural network system may further learn to determine the lesion types and to grade the lesions. Common retinal fundus lesions include diabetic retinopathy (see FIG. 2(*a*)), hypertensive retinopathy and arteriosclerotic retinopathy (see FIG. 2(*b*)), age-related macular degeneration, retinal vein occlusion, retinal artery occlusion, high myopia retinal fundus lesions, and even cardiovascular diseases related retinal fundus lesions and the like. The artificial neural network and the artificial neural network system according to this embodiment can are especially suitable for diagnosis of the diabetic retinopathy.

As mentioned above, the artificial neural network and the artificial neural network system according to this embodiment may be configured to output the diagnostic conclusions classified as "with lesion" or "without lesion", or alternatively classified as "without lesion" or "a certain lesion type". In addition, the diagnostic conclusion classification in the artificial neural network and network according to this embodiment may also be adjusted according to specific requirements.

In some examples, when such an artificial neural network or artificial neural network system is able to do the diagnosis as a retinal fundus doctor, or the diagnosis accuracy achieved by the artificial neural network or artificial neural network system (including sensitivity and specificity) meets a related diagnostic criteria, the artificial neural network or artificial neural network system can be used to assist a doctor with the diagnosis or to do part of a doctor's work. The artificial neural network and artificial neural network system according to this embodiment can save a lot of time of a doctor on retinal fundus lesion screening (film reading time) so that more people may get service on retinal fundus screening, thereby promoting the development of health care, especially the primary health care.

Furthermore, in addition to the lesions in retinal fundus images, the artificial neural network and artificial neural network system according to the present disclosure may also be used to recognize lesions in other medical images, where the medical images may be, for example, X-ray photographs, ultrasound images, CT images, OCT images, MRI images, fluorescence angiogram images and the like that are taken from human bodies or tissues.

Figure 3:
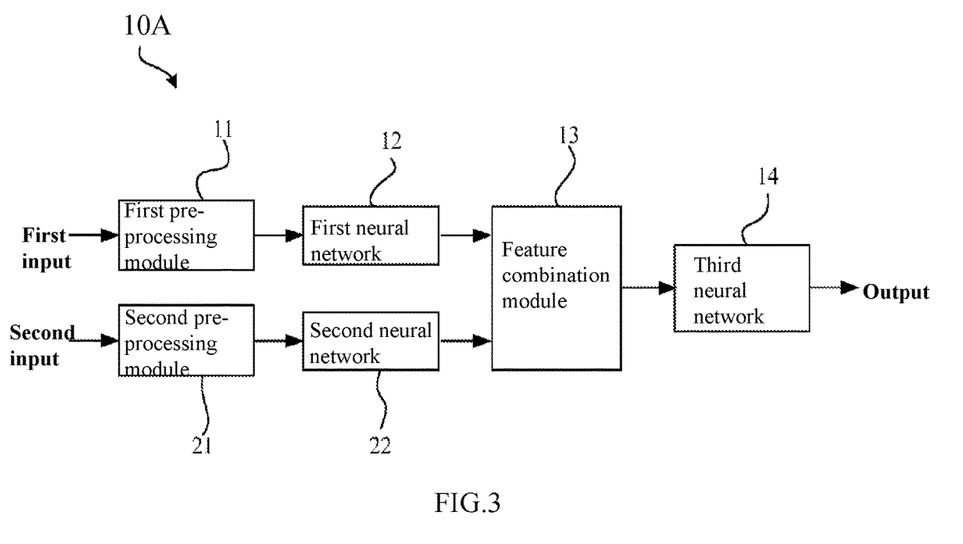
FIG. 3 is a schematic diagram showing an artificial neural network for identifying a lesion in a retinal fundus image according to the first embodiment of the present disclosure.

FIG. 3 is a schematic diagram showing an artificial neural network 10A for identifying a lesion in a retinal fundus image according to this embodiment. For example, as shown in FIG. 3, the artificial neural network 10A according to this embodiment may be used to recognize a lesion in a retinal fundus image. In particular, the artificial neural network 10A may recognize a lesion in a retinal fundus image by using a deep learning method.

It is well known that deep learning is one of machine learning methods, and the deep learning is based on characterization and study of data. In deep learning, low level features are combined to extract higher level representation attribute category or feature as to find the distributed feature representation of data By means of the deep learning, the accuracy of lesion recognition can be improved.

In this embodiment, the accuracy of lesion recognition can be reflected by sensitivity and specificity. Specifically, the screening result may be true negative, true positive, false negative and false positive. True negative refers to that an image shows normal retinal fundus and the screening report also indicates normal retinal fundus. True positive refers to that lesions are present in a retinal fundus image and the screening also reports the lesions. False negative refers to that lesions are present in a retinal fundus image, but the screening indicates normal retinal fundus. False positive refers to that an image shows normal retinal fundus, but the screening reports lesions. Thus, the sensitivity and the specificity are defined as follows, respectively:

$$\text{Sensitivity} = \frac{\text{True positives}}{\text{True positives} + \text{False negatives}} \times 100\%$$

$$\text{Specificity} = \frac{\text{True negatives}}{\text{True negatives} + \text{False positives}} \times 100\%$$

In general, the higher the sensitivity and specificity are, the higher lesion identification accuracy will be. According to some screening criteria, a screening model is sound when, for example, the sensitivity is over 80% and the specificity is 90%. In contrast, the artificial neural network and neural network system according to this embodiment may have a sensitivity of 85% or higher and a specificity of 90% or higher.

In this embodiment, lesions in retinal fundus images may include, but are not limited to, diabetic retinopathy, age-related macular degeneration, retinal vein occlusion and the like, and this embodiment may especially apply to the diabetic retinopathy.

Moreover, in this embodiment, the identification of lesions in a retinal fundus image may be achieved by rating. In some examples, a primary rating and a secondary rating may be employed. For example, a screening report provided by the artificial neural network 10A and the system thereof may be taken as the primary rating result, and then a doctor may make secondary rating based on the screening report. Therefore, a more accurate and reliable screening result can be obtained.

In this embodiment, a neural network structure employed in the artificial neural network 10A is not particularly restricted. In some examples, the artificial neural network 10A according to this embodiment may be designed as a deep neural network. For example, the first neural network 12 and the second neural network 22 may adopt the structure of a deep neural network. In this case, abstract image features may be extracted from a particular medical image (such as a retinal fundus image), thereby facilitating the lesion diagnosis.

As shown in FIG. 3, the artificial neural network 10A according to this embodiment may include a pre-processing module, a first neural network 12, a second neural network 22, and a feature combination module 13, and a third neural network 14. Here, the pre-processing module may specifically contain a first pre-processing module 11 and a second pre-processing module 21.

In this embodiment, the pre-processing modules (the first pre-processing module 11 and the second pre-processing module 21) may be configured to separately pre-process a target retinal fundus image and a reference retinal fundus image (a retinal fundus image pair) that are taken from the same person. That is, the first pre-processing module 11 may pre-process the target retinal fundus image, while the second pre-processing module 21 may pre-process the reference retinal fundus image. In addition, in this embodiment, the first pre-processing module 11 and the second pre-processing module 21 may be arranged as one module, or formed as separate modules.

As mentioned above, in this embodiment, a target retinal fundus image and a reference retinal fundus image taken from the same person are used as diagnosis inputs, that is, the target retinal fundus image as a first input and the reference retinal fundus image as a second input (see FIG. 3). As mentioned above, in this embodiment, the target retinal fundus image itself is used for the diagnosis of retinal fundus lesions in a target image, and a reference retinal fundus image is used as a diagnostic reference, which process simulates a real doctor who makes compares several retinal fundus images and use these images as a reference in diagnosis, which enhances the diagnosis accuracy.

In addition, in the artificial neural network 10A according to this embodiment, the inventors of the present disclosure also take the following facts into account: 1) images from the same person (the target retinal fundus image and the reference retinal fundus image) should give the same diagnosis result; 2) statistically, retinal fundus lesions on the left and the right eye of one person (patient) are similar. Therefore, when making a diagnosis on a target retinal fundus image, the diagnosis accuracy can be improved by using other retinal fundus image from the same patient as reference.

Moreover, during the training or testing process of the artificial neural network 10A, two retinal fundus images taken from a single eye (the left or right eye) of one person may be used in some examples. In this case, either of the two retinal fundus images may be used as the target retinal fundus image and the other as the reference retinal fundus image. In other examples, two retinal fundus images respectively from two eyes of one person may also be used. Similarly, in this case, either of the two retinal fundus images may be used as the target retinal fundus image and the other as the reference retinal fundus image.

Moreover, in the artificial neural network 10A according to this embodiment, in some examples, a target retinal fundus image and a reference retinal fundus image may be the same (that is, a first input and a second input may be the same). In this case, even though only one retinal fundus image taken from a patient is used by the artificial neural network 10A according to this embodiment during the training or testing process, this retinal fundus image may be used as the target retinal fundus image and the reference target retinal fundus separately. Thus, a valid lesion diagnosis result can also be obtained.

Moreover, four retinal fundus images, including two retinal fundus images taken from a left eye and two retinal fundus images taken from a right eye, may also be used in this embodiment. In this case, any one of the four retinal fundus images may be used as the target retinal fundus images and the others as the reference retinal fundus images.

In addition, in some examples, a plurality of retinal fundus images may be obtained during the retinal fundus image capture process. In this case, any one of the retinal fundus images may be used as the target retinal fundus images and the others as the reference retinal fundus images. In other examples, the same number of left eye retinal fundus images and right eye retinal fundus images may be used.

Moreover, retinal fundus images (including target retinal fundus images or reference retinal fundus images) used in this embodiment are not particularly restricted and the retinal fundus images can be color images (such as RGB images), and may also be grayscale images.

In this embodiment, a retinal fundus image pair consisting of a target retinal fundus image and a reference retinal fundus image is used as inputs (including a first input and a second input). In this case, since the target retinal fundus image and the reference retinal fundus image (the retinal fundus image pair) are similar or the same, therefore, the screening capability of the artificial neural network can be improved by inputting the target retinal fundus image and the reference retinal fundus image separately to a first neural network and a second neural network respectively (that is, the target retinal fundus image is used as the first input in the first neural network, and the reference retinal fundus image as the second input in the second neural network, as shown in FIG. 3) to extract features of the retinal fundus images.

Moreover, in the artificial neural network 10A according to this embodiment, a target retinal fundus image and a reference retinal fundus image may be from different eyes. In this case, it may help to improve the artificial neural network 10A via training such that the trained artificial neural network 10A may work in a way close to real diagnosis.

(Pre-Processing Module)

Figure 4:
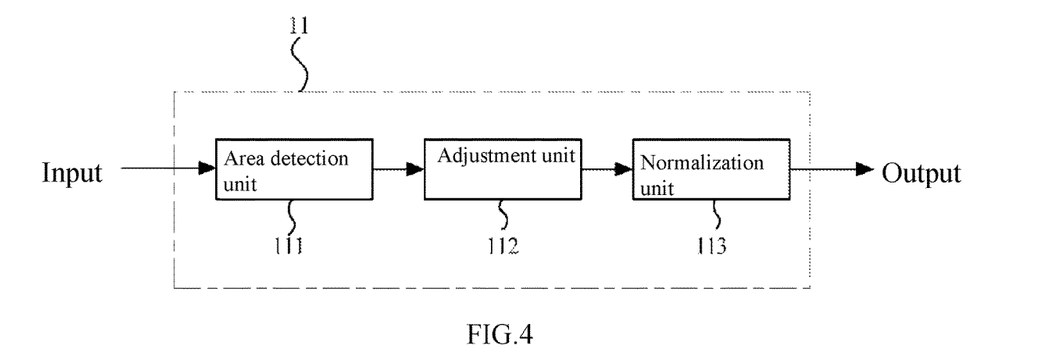
FIG. 4 is a block diagram showing the pre-processing module of the artificial neural network according to the first embodiment of the present disclosure.

FIG. 4 is a block diagram showing a pre-processing module of the artificial neural network 10A according to this embodiment.

As mentioned above, the pre-processing module (including a first pre-processing module 11 and a second pre-processing module 21) may be configured to separately pre-process a target retinal fundus image and a reference retinal fundus image (a retinal fundus image pair) that are taken from one person. In particular, the first pre-processing module 11 and the second pre-processing module 21 may perform pre-processing such as retinal fundus area detection, image clipping resizing, normalizing and the like, for retinal fundus images. That is, the first pre-processing module 11 may perform retinal fundus area detection, image clipping, resizing, normalizing, and the like for the target retinal fundus image, and the second pre-processing module 21 may perform retinal fundus area detection, image clipping, resizing, normalizing, and the like for the reference retinal fundus image.

In this embodiment, since the first pre-processing module 11 and the second pre-processing module 21 may be set as the same. Therefore, only the first pre-processing module 11 will be described below in detail, and the second pre-processing module 21 may be completely the same in structure with the first pre-processing module 11.

As shown in FIG. 4, the first pre-processing module 11 of the artificial neural network 10A mainly includes an area detection unit 111, an adjustment unit 112 and a normalization unit 113.

In the first pre-processing module 11, the area detection unit 111 can determine the area with retinal fundus from various retinal fundus images. In this embodiment, a retinal fundus area to be detected may be, for example, a retinal fundus area with the optic disc at the center, or a retinal fundus area comprising the optic disc with the macula lutea at the center. In this embodiment, any area, whether with the optic disc at the center or comprises the optic disc and with the macula lutea at the center, can show retinal fundus lesions effectively. In some examples, the area detection unit 111 can detect a specific area in a retinal fundus image by, for example, a sampling threshold method or Hough transform, for later use by the artificial neural network. For example, referring to the retinal fundus images shown in FIG. 1(a) and FIG. 1(b) and the like, the brightest circle in the retinal fundus image is the optic disc, and the darkest area is the macula lutea or fovea centralis, together with blood vessels from the optic disc.

In addition, as shown in FIG. 4, the adjustment unit 112 may be configured to clip and resize a retinal fundus image (a target retinal fundus image). Due to different sizes of the human eyes and different retinal fundus camera devices as used, the obtained retinal fundus images may vary in resolution, retinal fundus area size and the like. Therefore, it is necessary to resize such retinal fundus images. For example, with the adjustment unit 112, a retinal fundus image may be clipped according to a given specification. In some examples, a square retinal fundus image may be obtained by clipping. Moreover, a retinal fundus image in this embodiment is not limited to square, and may also be, for example, rectangular, round, oval and the like. Further, the adjustment unit 112 can also perform other processing on a retinal fundus image including, for example, distinguishing a retinal fundus area from a patient information area in a single retinal fundus image (some retinal fundus images may contain names, medical insurance numbers and the like), and resizing retinal fundus images processed by different retinal fundus camera devices using different algorithms to result in the same background intensity among images.

In addition, in some examples, the adjustment unit 112 can resize a retinal fundus image to a specified size (e.g., pixel size), such as 256×256, 512×512, 1024×1024 pixels and the like. However, this embodiment is not limited thereto, and depending on particular requirements, the size of a retinal fundus image can also be other specified sizes (pixel size), such as 128×128, 768×768, 2048×2048 pixels and the like.

Although there are no limitations to the size of a retinal fundus image in this embodiment, to more accurately identify more details in a retinal fundus image, the size of a retinal fundus image in this embodiment is preferably higher than or equal to 512×512 pixels. The deep learning framework Inception-v3 involved in the patent document 1 as mentioned above uses an image of only 299×299 pixels. However, since the feature(s) of many retinal fundus diseases (such as the features of the diabetic retinopathy at an early phase) may not be obviously shown at such a pixel level, it may result in loss of important image detail information, for example, loss of low-grade retinal fundus lesion (such as the grade 1 diabetic retinopathy) information during the subsequent down-sampling process (especially in a down-sampling where data is reduced to a great extent). Accordingly, in the patent document 1, the grade 1 diabetic retinopathy may be deemed as a healthy eye, which may thus lead to inaccurate diagnosis and poor clinical effect. In contrast, in this embodiment, by defining the size of a retinal fundus image as described above, the loss of detail information in a retinal fundus image can be effectively inhibited, thus improving diagnosis accuracy.

In addition, in the first pre-processing module 11, the normalization unit 113 may be configured to normalize a retinal fundus image (a target retinal fundus image). Due to retinal fundus differences among different races and retinal fundus imaging devices or conditions, retinal fundus images may greatly vary, and therefore, it is necessary to perform normalization processing on the images.

In this embodiment, the normalization way of the normalization unit 113 is not particularly restricted. For example, zero mean, unit standard deviation and the like may be adopted for normalization. In addition, in some examples, the normalization may be done within the range of [0, 1]. By normalization, the difference among different retinal fundus images can be eliminated and the performance of the artificial neural network can be improved.

Figure 5:
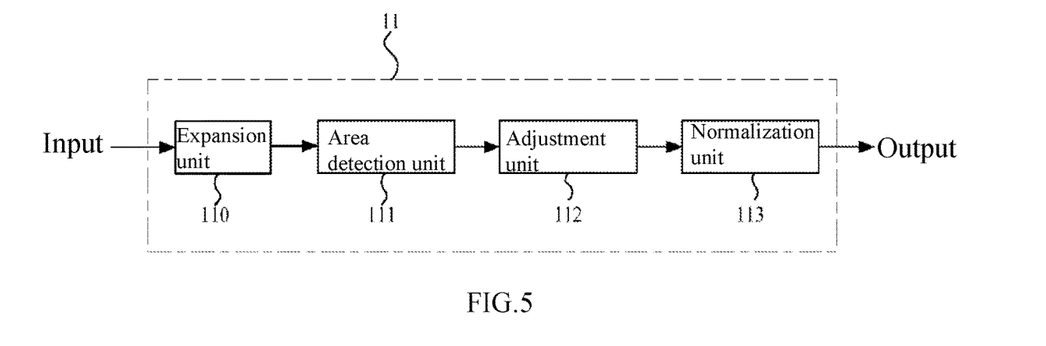
FIG. 5 is a schematic diagram showing another pre-processing module in FIG. 4.

FIG. 5 is a schematic diagram showing another pre-processing module 11 according to this embodiment. As shown in FIG. 5, the first pre-processing module 11 may further contain an expansion unit 110. The expansion unit 110 may be arranged ahead of the area detection unit 111, which arrangement is not limiting.

In this embodiment, the expansion unit 110 may be configured to expand retinal fundus image data at the training phase of the neural network. With the expansion unit 110, data expansion may be performed for an obtained retinal fundus image (a target retinal fundus image) by increasing retinal fundus image sample size, thereby overcoming the over-fitting problem and improving the performance of the artificial neural network. In addition, what needs to be noted is that the expansion unit 110 is generally used to expand data samples at the training phase of the neural network (will be described later) but not used at the testing phase of the neural network.

In addition, there are no particular limitations to the expansion way taken by the expansion unit 110. For example, in some examples, sample expansion may be achieved through various image transformation of a retinal fundus image. Such image transformation may include symmetric transformation, inverse transformation, rotation transformation, pixel translation and the like, and may also include adjustment of contrast, brightness, color, sharpness and the like of an image.

The configuration and function of the first pre-processing module 11 have been described above. Similarly, the second pre-processing module 21 may also have the same configuration and function with the first pre-processing module 11. In this case, a reference retinal fundus image as a second input can be effectively pre-processed through the second pre-processing module 21, so that the artificial neural network (the second neural network and the third neural network) can process the reference retinal fundus image subsequently.

As mentioned above, a target retinal fundus image and a reference retinal fundus image can be effectively pre-processed, respectively, by means of the first pre-processing module 11 and the second pre-processing module 21, thereby facilitating subsequent further processing (such as feature extraction and the like) on retinal fundus images by each neural network.

(First/Second Neural Network)

In this embodiment, the first neural network 12 may be configured to generate a first advanced feature set from a pre-processed target retinal fundus image. Similarly, the second neural network 22 may be configured to generate a second advanced feature set from a pre-processed reference retinal fundus image. The first neural network and the second neural network may achieve abstract description of the target retinal fundus image and the reference retinal fundus image by, for example, combining multiple layers of low-level features (pixel-level features). Here, the advanced features are termed relative to primary features (e.g., pixel-level features), referring to the features processed by the artificial neural network. However, in general, after being processed by the neutral network, the features tend to be in a higher level and more abstract as deeper layers of the neutral network get involved. In addition, a feature set generally contains two or more features, and may sometimes be referred to as a "feature matrix" in the present disclosure. Moreover, in some special cases, a feature set may also contain only one feature, such as an intermediate result, and accordingly the "feature set" may refer in particular to a single "feature".

In addition, in this embodiment, the first neural network 12 and the second neural network 22 may both be designed as a convolutional neural network (CNN). Due to the advantages of weight-sharing, local receptive field and the like of the convolutional neural network, training of parameters can be greatly shortened or decreased, therefore increasing processing speed and saving hardware cost. Additionally, the convolutional neural network can perform image identification more effectively.

Figure 6:
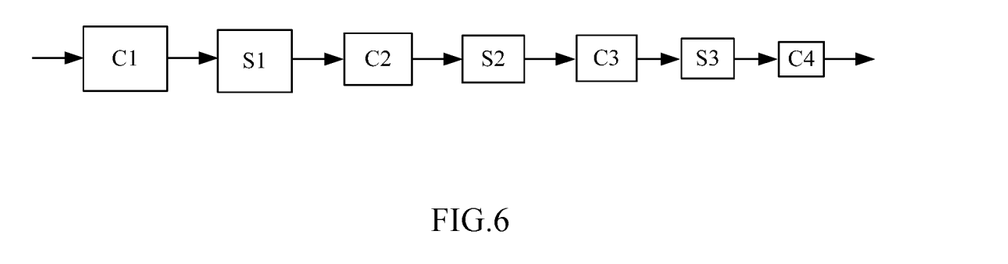
FIG. 6 is a schematic diagram showing an exemplary network structure of the artificial neural network according to the first embodiment of the present disclosure.
Figure 7:
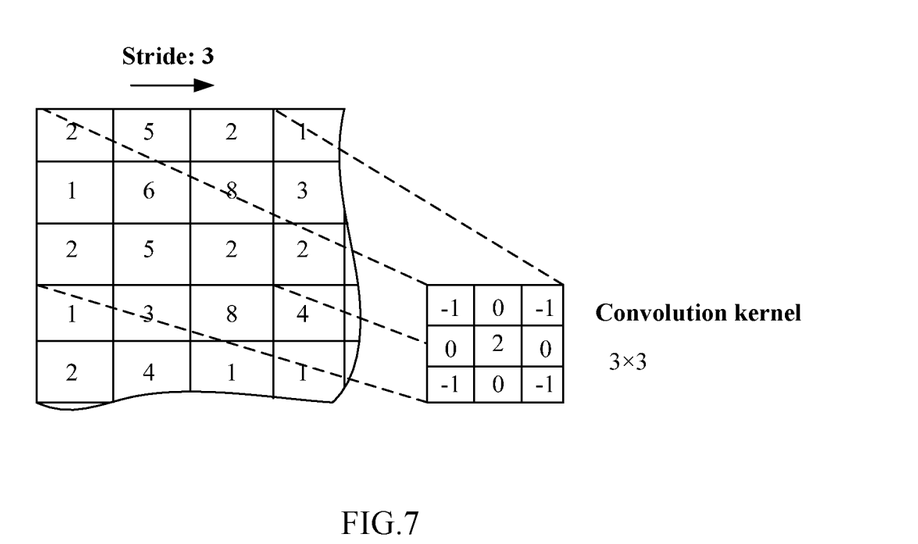
FIG. 7 is a schematic diagram showing an exemplary convolution kernel employed in the artificial neural network in FIG. 6.

FIG. 6 is a schematic diagram showing an exemplary network structure of the artificial neural network according to the first embodiment of the present disclosure. FIG. 7 is a schematic diagram showing an exemplary convolution kernel employed in the artificial neural network of FIG. 6.

In some examples, the first neural network 12 and the second neural network 22 may be both convolutional neural networks. For example, the network structures of the first neural network 12 and the second neural network 22 may be designed to have the neural network structures as shown in FIG. 6 and FIG. 7 (simplified representation):

C1-S1-C2-S2-C3-S3-C4-

Here, C (including C1, C2, C3, and C4) represents a convolutional layer, and S (including S1, S2, and S3) represents a pooling layer (sometimes referred to as a "down-sampling layer"). In some examples, the layer C1 uses a 5×5 convolution kernel, and each of the other convolutional layers may use a 3×3 convolution kernel. In this case, the use of a medical image (a retinal fundus image) of a specified size, such as in 256×256 or 512×512 pixels may greatly decrease parameter training and thus improve the training efficiency.

In addition, in the above convolutional neural network, the way of pooling may be max-pooling, mean-pooling, stochastic-pooling, and the like. The pooling operation, on one hand, may reduce dimensionality and improve operation efficiency. Additionally, the neural network can be enabled to extract more abstract high-level features, thereby improving the diagnosis accuracy.

In addition, in the above convolutional neural network, the number of convolutional layers and the number of pooling layers may also be increased according to actual need. In this case, the neural network can also be enabled to extract more abstract high-level features to further improve the diagnosis accuracy.

In addition, in the artificial neural network 10A according to this embodiment, the first neural network 12 and the second neural network 22 may be completely the same. Specifically, the network structure of the first neural network 12 and the network structure of the second neural network 22 may be completely the same. In this case, the number of parameters of the artificial neural network can be reduced, thereby inhibiting over-fitting in the neural network.

In addition, the convolutional neural network structure used for the first neural network 12 and the second neural network 22 is not limited thereto, and other convolutional neural network structures can also be adopted as long as advanced features can be extracted from original retinal fundus images (a target retinal fundus image and a reference retinal fundus image). Moreover, it is noted that the first neural network 12 and the second neural network 22 according to this embodiment are mainly intended for feature extraction and not for directly outputting a lesion diagnosis result.

(Feature Combination Module)

In this embodiment, as shown in FIG. 3, the feature combination module 13 may be configured to combine a first advanced feature set generated by the first neural network 12 and a second advanced feature set generated by the second neural network 22 to form a feature combination set. Here, the "feature set" in this embodiment may refer to a "feature sequence", a "feature vector", a "feature value set" and the like, and the meaning thereof should be understood in the broadest manner.

In some examples, the feature combination module 13 may combine a first advanced feature set and a second advanced feature set to form a one-dimensional feature vector (a feature combination set). In addition, in other examples, the feature combination module 13 may also determine differences between a first advanced feature set and a second advanced feature set to obtain a feature combination set. Further, in other examples, the feature combination module 13 may also calculate mean values of a first advanced feature set and a second advanced feature set to obtain a feature combination set. Further, in other examples, the feature combination module 13 may perform linear or nonlinear transformation on a first advanced feature set and a second advanced feature set to obtain a feature combination set.

In this embodiment, the features generated from the first neural network 12 and the features generated from the second neural network 22 can be combined by the feature combination module 13, thereby facilitating subsequent processing in the third neural network 14.

(Third Neural Network)

In this embodiment, the third neural network 14 may be configured to generate a diagnostic report according to the feature combination (a feature combination set). As shown in FIG. 3, the third neural network 14 may produce a diagnostic report for the input target retinal fundus image based on the processing result from the feature combination module 13. That is, the third neural network 14 generates a diagnosis result according to the feature combination set.

In this embodiment, the output dimensions of the third neural network 14 are consistent with the conclusive lesion category (e.g., a lesion type). That is, for example, when the diagnostic conclusion indicates "with lesion" or "without lesion", the output dimensions of the third neural network 14 may be 2; and if the diagnostic conclusion is classified to "without lesion" and specific lesion types (e.g., 5 lesion types), the output dimensions of the third neural network 14 may be 6. In addition, the output dimensions of the third neural network 14 can be adjusted according to the actual situation.

In some examples, the outputs of the third neural network 14 may be values (percentages) between 0 and 1, and such values may each be interpreted as the probability of being classified into a particular category (lesion type). Then, the sum of the output values of the third neural network 14 is 1 (probability sum).

In this embodiment, the probability values output by the third neural network 14 are used for making a final diagnostic conclusion. In some examples, the retinal fundus is determined to have a specific lesion with the highest probability value. For example, if the probability value is highest for "lesion-free", then the retinal fundus is determined to be lesion-free. If the probability value is highest for diabetic retinopathy, then the retinal fundus in the target image is determined to have diabetic retinopathy.

In addition, the network structure of the third neural network 14 is not particular restricted. In some examples, the third neural network 14 may use a convolutional layer, a fully connected layer and some auxiliary layers (such as a batch normalization layer, a pooling layer and the like). For example, in some cases, the output layers of the third neural network 14 may comprise a single convolutional layer, two fully connected layers and an output layer (softmax layer). Moreover, in other cases, the output layers of the third neural network 14 may adopt two convolutional layers, two pooling layers, three fully connected layers, and an output layer (e.g., a softmax layer).

As mentioned above, in this embodiment, using a target retinal fundus image and a reference retinal fundus image as independent input information facilitates extraction of advanced features from the target retinal fundus image by the first neural network and extraction of advanced features from the reference retinal fundus image by the second neural network. Furthermore, the advanced features that are obtained from the first neural network and the second neural network respectively are combined and then a diagnosis result is obtained via the third neural network. Thus, the diagnostic performance can be significantly improved.

(Training and Testing)

In this embodiment, the first neural network 12, the second neural network 22 and the third neural network 14 can be trained together to obtain an optimal neural network structure. For example, retinal fundus image pairs (each with a target retinal fundus image and a reference retinal fundus image) from a training set can be used for the training of neural networks comprising convolutional neural networks as a first neural network 12 and a second neural network 22.

Moreover, as described, the first neural network 12, the second neural network 22 and the third neural network 14 according to this embodiment can be trained together, but the embodiment is not limited thereto. For example, the first neural network 12 and the second neural network 22 may be trained first by means of auto-encoder network training and then be trained together with the third neural network 14.

In addition, in this embodiment, for the retinal fundus images, during the training or testing process of the artificial neural network 10A, two retinal fundus images of a single eye may be used, and two retinal fundus images each of one eyes from one person may also be used.

Furthermore, during the training or testing process of the artificial neural network 10A, four retinal fundus images comprising two retinal fundus images taken from the left eye and two retinal fundus images taken from the right eye may also be used, which may better match the actual situation of lesion diagnosis using retinal fundus images. Incidentally, the international lesion diagnosis standard using retinal fundus images at present is using seven retinal fundus images covering different retinal fundus areas with a visual angle of 30 degrees. However, the inventors of the present disclosure have found in long-term practice that an equivalent lesion diagnosis effect may also be achieved by using, for example, four retinal fundus images from two eyes covering specified areas with a visual angle of 45 degrees.

Additionally, this embodiment is not limited thereto, and more retinal fundus images taken from two eyes of one person may also be used. More preferably, a certain number of retinal fundus images taken from left eye and an equal number of images from the right eye can be used.

During the training process of the artificial neural network 10A according to this embodiment, 50,000-200,000 retinal fundus images from a cooperative hospital, the patient information of which have been removed, may form a training set, and 5,000-20,000 retinal fundus images may form a testing set. During the training or testing process, the retinal fundus images are unified to RGB color retinal fundus images in a size of, for example, 512×512 or 1024× 1024 pixels.

During the training process, parameters are adjusted by using the stochastic gradient descent method, to obtain a final training result. Then, the trained artificial neural network 10A is employed to identify lesions from retinal fundus images in the testing set, with an average identification accuracy of, for example, 90% and more. It thus can be seen that the artificial neural network 10A according to this embodiment can obtain an improved lesion diagnosis accuracy with consideration of the retinal fundus clinical circumstance.

(Lesion Identification Process)

Figure 8:
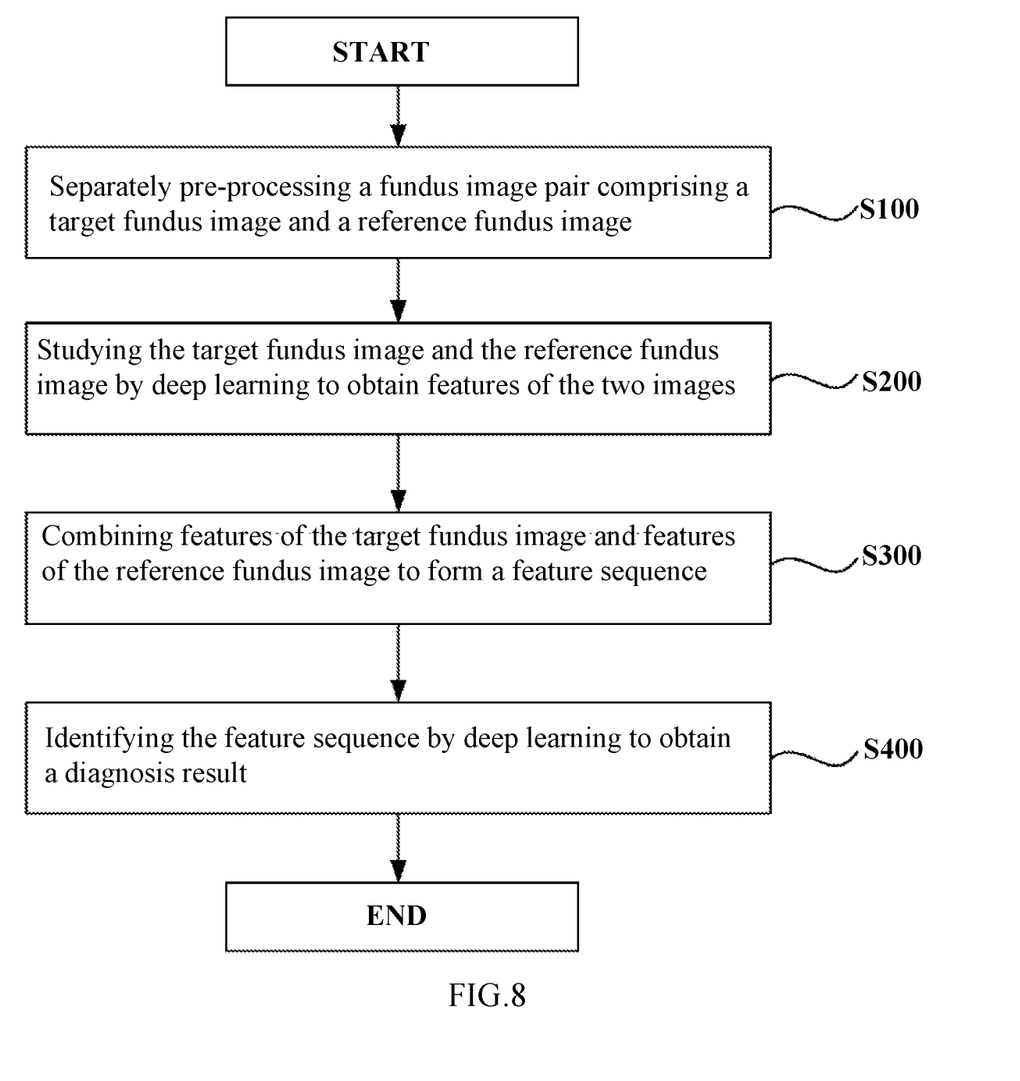
FIG. 8 is a block diagram of an artificial neural network system according to the first embodiment of the present disclosure.

FIG. 8 is a flowchart showing a method for identifying a lesion in a retinal fundus image using the artificial neural network 10A according to this embodiment. Hereinafter, with reference to FIG. 8, the method for identifying a lesion in a retinal fundus image using the artificial neural network 10A according to this embodiment will be described below in detail.

In the method for identifying a lesion in a retinal fundus image according to this embodiment, first, separate pre-processing is performed on a retinal fundus image pair comprising a target retinal fundus image and a reference retinal fundus image (step S100) to obtain retinal fundus images meeting certain requirements.

In step S100, for example, area detection, image clipping, resizing, normalization and the like may be performed on the retinal fundus image. In addition, in step S100, data expansion may also be performed using the retinal fundus image pair (including the target retinal fundus image and the reference retinal fundus image) during neural network training to increase the size of data samples for training, thereby improving the diagnosis accuracy. In some examples, the target retinal fundus image and the reference retinal fundus image may be the same image.

Then, after step S100, separate operations may be performed on the target retinal fundus image and the reference retinal fundus image by using the deep learning method so as to obtain the features of the target retinal fundus image and the features of the reference retinal fundus image (step S200). In step S200, advanced features of the target retinal fundus image and advanced features of the reference retinal fundus image may be obtained by means of, for example, convolutional neural network. Since the convolutional neural network has the advantages of local receptive field and weight-sharing and is good for extraction of advanced features of a retinal fundus mage, the operation efficiency can be improved and the hardware cost can be saved.

After step S200, the features of the target retinal fundus image and the features of the reference retinal fundus may be combined to form a feature combination set (step S300). As described above, forming a feature combination set is beneficial for the combination of the features of the target retinal fundus image and the features of the reference retinal fundus image, thereby facilitating subsequent classification and diagnosis.

Finally, the feature combination set may be studied via a deep learning method so as to obtain a diagnosis result (step S400). In step S400, the diagnosis result may be obtained by using, for example, an average operator, a maximum operator, logistic regression, random forest, and a support vector machine (SVM) and the like.

(Artificial Neural Network System)

Figure 9:
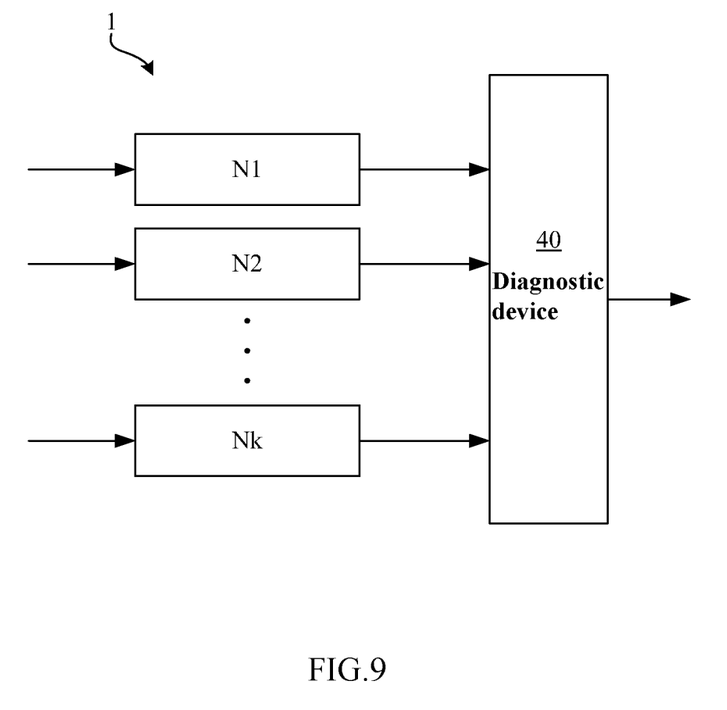
FIG. 9 is a flowchart showing a method for identifying a lesion in a retinal fundus image by the artificial neural network according to the first embodiment of the present disclosure.

FIG. 9 is a block diagram of an artificial neural network system 1 according to the first embodiment of the present disclosure.

In this embodiment, as shown in FIG. 8, a plurality of artificial neural networks Ni ($1 \leq i \leq k$), such as artificial neural network N1, artificial neural network N2, artificial neural network N3 . . . , and artificial neural network Nk ($k \geq 2$), and a diagnostic device 40 may be arranged to form an artificial neural network system 1. That is, the artificial neural network system 1 may contain a plurality of artificial neural networks (the above artificial neural network N1, artificial neural network N2, artificial neural network N3 . . . , and artificial neural network Nk), and a diagnostic device 40. The above artificial neural networks (artificial neural network N1, artificial neural network N2, artificial neural network N3 . . . , artificial neural network Nk) may each be the artificial neural network 10A.

In this embodiment, inputs to the artificial neural network Ni ($1 \leq i \leq k$) may be a target retinal fundus image and a reference retinal fundus image (a retinal fundus image pair) from one eye of one person.

In addition, in some examples, each artificial neural network Ni ($1 \leq i \leq k$) may be the artificial neural network 10A. In particular, an artificial neural networks 10A that uses the same retinal fundus image pair may be used as the artificial neural networks Ni ($1 \leq i \leq k$).

In this embodiment, the diagnostic device 40 may combine the results from the above plurality of artificial neural network Ni ($1 \leq i \leq k$) and then output a final diagnosis result. That is, the outputs from the above plurality of artificial neural networks (the above artificial neural network N1, artificial neural network N2 . . . , and artificial neural network Nk) are input to the diagnostic device 40, and the diagnostic device 40 combines these outputs and comes to the final diagnosis result.

In some examples, the diagnostic device 40 may output a diagnosis result indicating the presence or absence of a disease. In other examples, the diagnostic device 40 may output a diagnosis result indicating the presence or absence of a disease and further a specific lesion type in the case of disease presence.

In some examples, the diagnostic device 40 may output a probability value as the basis of the diagnosis result. In addition, the method used by the diagnostic device 40 may be various linear or nonlinear classifiers, such as Logistic Regression, Random Forest, Support Vector Machine (SVM), Adaboost and the like. In some examples, the diagnostic device 40 may also adopt some simple numerical operators, such as Average Operator, Maximum Operator and the like.

Second Embodiment

Figure 10:
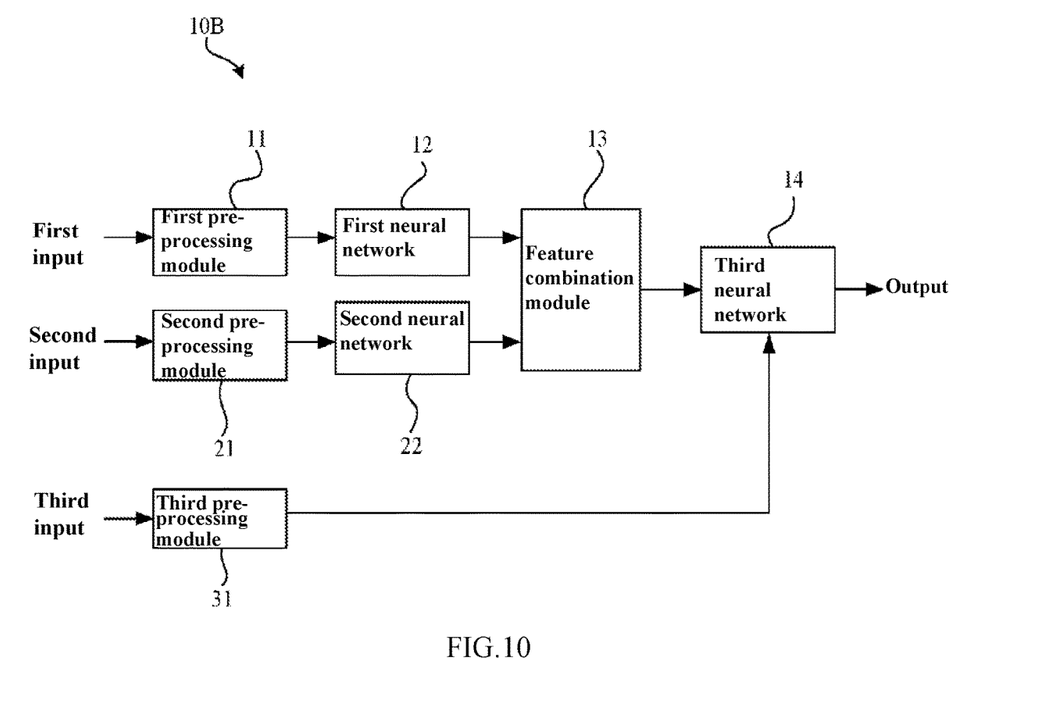
FIG. 10 is a block diagram showing an artificial neural network according to a second embodiment of the present disclosure.
Figure 11:
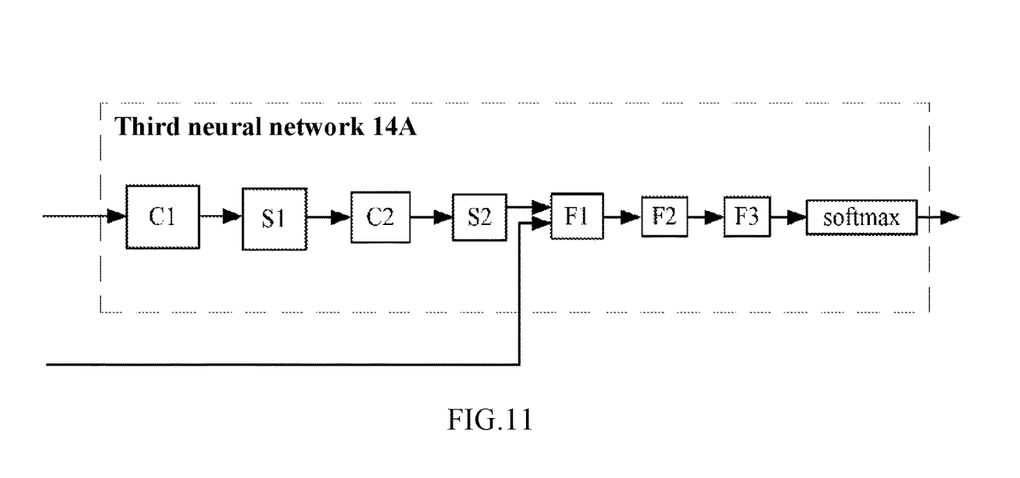
FIG. 11 is a schematic diagram illustrating a third neural network according to the second embodiment of the present disclosure.
Figure 12:
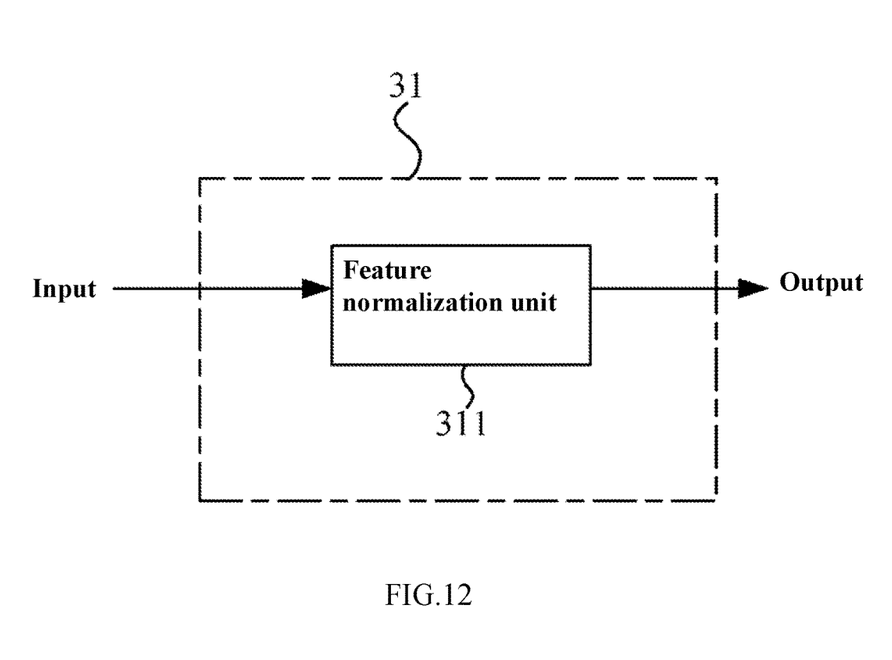
FIG. 12 is a block diagram showing a pre-processing module of the artificial neural network according to the second embodiment of the present disclosure.

FIG. 10 is a block diagram showing an artificial neural network 10B according to the second embodiment of the present disclosure. FIG. 11 is a diagram illustrating a third neural network 14 according to the second embodiment of the present disclosure. FIG. 12 is a block diagram showing a pre-processing module 31 of the artificial neural network 10B according to the second embodiment of the present disclosure.

The difference between the artificial neural network 10B according to this embodiment and the artificial neural network 10A according to the first embodiment is that the artificial neural network 10B comprises a pre-processing module 31, and the third neural network 14 may generate a diagnosis result according to the feature combination set and patient information (see FIG. 10). The artificial neural network 10B according to this embodiment can also improve the accuracy (including sensitivity and specificity) of screening of retinal fundus lesions.

The feature combination set has been described in detail in the first embodiment, and its description will be omitted here. In this embodiment, the feature combination set obtained by the feature combination module 13 is input into the third neural network 14. Further, the third neural network 14 generates a diagnosis result according to the feature combination set and patient information.

In this embodiment, the output dimensions of the third neural network 14 are consistent with the conclusive lesion category (e.g., a lesion type). That is, for example, when the diagnostic conclusion indicates "with lesion" or "without lesion", the output dimensions of the third neural network 14 may be 2; and if the diagnostic conclusion is classified to "without lesion" and specific lesion types (e.g., 5 lesion types), the output dimensions of the third neural network 14 may be 6. In addition, the output dimensions of the third neural network 14 can be adjusted according to the actual situation.

In some examples, the outputs of the third neural network 14 may be values (percentages) between 0 and 1, and such values may each be interpreted as the probability of being classified into a particular category (lesion type). Then, the sum of the output values of the third neural network 14 is 1 (probability sum).

In this embodiment, the probability values output by the third neural network 14 are used for making a final diagnostic conclusion. In some examples, the retinal fundus is determined to have a specific lesion with the highest probability value. For example, if the probability value is highest for "lesion-free", then the retinal fundus is determined to be lesion-free. If the probability value is highest for diabetic retinopathy, then the retinal fundus in the target image is determined to have diabetic retinopathy.

In addition, in some examples, the patient information contains at least one of a patient's eyesight, age, gender, and medical history. Moreover, the patient information may also contain body weight. According to the findings of the inventors of the present disclosure in years of ophthalmic practice, a patient's eyesight, age, gender, medical history, body weight and the like are all closely related to retinal fundus lesions. That is, factors such as a patient's eyesight, age, gender, medical history and the like are also important reference factors for retinal fundus lesion diagnosis.

Furthermore, the artificial neural network 10B may contain a third pre-processing module 31 by which the patient information may be pre-processed. The third pre-processing module 31 may contain a feature normalization unit 311 by which, for example, the values representing the patient information can be normalized to an interval of [0, 1], thereby avoiding bad effects of the patient information on subsequent processing by the neural network.

In this embodiment, patient information is considered by the artificial neural network 10B and provided as a third input to the third neural network 14A so as to improve the lesion recognition capability of the artificial neural network 10B. In the third neural network 14, in addition to the features output by the feature combination module 13, patient information is also input as features to the third neural network 14. Therefore, the third neural network 14 can generate a diagnosis result according to the feature combination set and the patient information.

In addition, the network structure of the third neural network 14 is not particularly restricted. In some examples, the third neural network 14 may be formed by combining a convolutional layer, a fully connected layer and other auxiliary layers (such as a batch normalization layer, a pooling layer and the like) in various ways. For example, in some cases, the output layers of the third neural network 14 may contain a single convolutional layer, two fully connected layers and an output layer (e.g., softmax layer). Moreover, in other cases, the output layers of the third neural network 14 may contain two convolutional layers, two pooling layers, three fully connected layers, and an output layer such as a softmax layer (see FIG. 11).

Furthermore, in this embodiment, the third neural network 14 may contain a fully connected layer, and patient information is used as inputs to the fully connected layer. In particular, for example, when the third neural network 14 contains a convolution layer, a pooling layer and a fully connected layer, patient information may be used as inputs to the fully connected layer (see FIG. 11). In this embodiment, when the third neural network 14 has a plurality of fully connected layers, patient information may be used as inputs to the first fully connected layer, and may also be used as inputs to any one of the other fully connected layers. In this case, the artificial neural network 10B performs diagnosis using the combination of retinal fundus image information (feature combination information) and patient information, which is close to the actual clinical diagnostic process of a doctor, and therefore, the accuracy of lesion in a retinal fundus image can be improved.

It should be noted that while different method examples as mentioned before are described as a combination of a series of operations for the sake of simple description, those skilled in the art will understand that the present disclosure is not limited to the described sequence of operations because some steps may be performed in other sequences or simultaneously according to the present application.

In the above embodiments or examples, the description of each embodiment or example has a focus, and the parts that are not described in detail in a certain embodiment or example may refer to related descriptions of other embodiments or examples.

In addition, the method steps according to the present disclosure may be sequentially adjusted, merged, and deleted according to actual needs. Units or subunits in the apparatus according to the present disclosure may be merged, divided, and deleted according to actual needs.

One of ordinary skill in the art can understand that all or part of the steps in the above embodiments can be completed by a program to instruct related hardware, and the program can be stored in a computer readable storage medium. The storage medium includes Read-Only Memory (ROM), Random Access Memory (RAM), Programmable Read-only Memory (PROM), and Erasable Programmable Read Only Memory (EPROM), One-time Programmable Read-Only Memory (OTPROM), Electrically-Erasable Programmable Read-Only Memory (EEPROM), Compact Disc Read-Only Memory (CD-ROM) or other optical disc storage, disk storage, magnetic tape storage, or any other medium readable by a computer that can be used to carry or store data.

While the present disclosure is described above in detail in combination with the drawings and embodiments, it will be understood that the above descriptions do not limit the disclosure in any form. The present disclosure may be modified and changed as needed by those skilled in the art without departing from the spirit and scope of the disclosure, and such modifications and variations are within the scope of the disclosure.

What is claimed is:

1. A system for recognizing a lesion in a fundus images, comprising:
   a pre-processing module, configured to separately pre-process a target retinal fundus image and a reference retinal fundus image taken from a same person;
   a first neural network, configured to generate a first advanced feature set from the target retinal fundus image;
   a second neural network, configured to generate a second advanced feature set from the reference retinal fundus image;
   a feature combination module, configured to combine the first advanced feature set and the second advanced feature set to form a feature combination set; and
   a third neural network, configured to generate, according to the feature combination set, a diagnosis result;
   wherein:
       the target retinal fundus image is an image of one eye of one person;
       the reference retinal fundus image is an image of the other eye of the person; and
       fundus images of a same resolution are used during a training process of the system.

2. The system according to claim 1, wherein the first neural network and the second neural network are the same.

3. The system according to claim 1, wherein the pre-processing module comprises:
   an area detection unit, configured to detect a designated retinal fundus area in the target retinal fundus image and in the reference retinal fundus image;
   an adjustment unit, configured to clip and resize the target retinal fundus image and the reference retinal fundus image; and
   a normalization unit, configured to normalize the target retinal fundus image and the reference retinal fundus image.

4. The system according to claim 1, wherein the third neural network generates the diagnosis result based on the feature combination set and patient information.

5. The system according to claim 4, wherein the patient information comprises at least one of age, gender, eyesight, and medical history.

6. The system according to claim 1, wherein the first neural network and the second neural network are both convolutional neural networks.

7. A system for identifying a lesion in a medical images, comprising:
   a pre-processing module, configured to separately pre-process a target medical image and a reference medical image taken from a same person;
   a first neural network, configured to generate a first advanced feature set from the target medical image;
   a second neural network, configured to generate a second advanced feature set from the reference medical image;
   a feature combination module, configured to combine the first advanced feature set and the second advanced feature set to form a feature combination set; and
   a third neural network, configured to generate a diagnosis result from the feature combination set;
   wherein:
       the target medical image is an image of one eye of one person;
       the reference medical image is an image of the other eye of the person; and
       medical images of a same resolution are used during a training process of the system.

8. A system comprising:
   a plurality of artificial neural networks, each being selected from the group consisting of a first neural network, a second neural network, and a third neural network; and
   a diagnostic device, configured to combine results output from the plurality of artificial neural networks and output a final diagnosis result;
   wherein:
       the first neural network, configured to generate a first advanced feature set from a target medical image;
       the second neural network, configured to generate a second advanced feature set from a reference medical image;
       the third neural network, configured to generate, according to a feature combination set, a diagnosis result; and
       medical images of a same resolution are used during a training process of the system.

9. The system according to claim 8, wherein the first neural network and the second neural network are the same.

10. The system according to claim 8, wherein the pre-processing module comprises:
    an area detection unit, configured to detect a designated medical area in the target medical image and in the reference medical image;
    an adjustment unit, configured to clip and resize the target medical image and the reference medical image; and
    a normalization unit, configured to normalize the target medical image and the reference medical image.

11. The system according to claim 8, wherein the third neural network generates the diagnosis result based on the feature combination set and patient information.

12. The system according to claim 11, wherein the patient information comprises at least one of age, gender, eyesight, and medical history.

13. The system according to claim 8, wherein the first neural network and the second neural network are both convolutional neural networks.

* * * * *